United States Patent
Jouanique-Dubuis et al.

(10) Patent No.: US 8,786,858 B2
(45) Date of Patent: Jul. 22, 2014

(54) GAS DETECTOR

(75) Inventors: Cécile Jouanique-Dubuis, Evrange (FR); Yves Decoster, Ethe (BE)

(73) Assignee: IEE International Electronics & Engineering S.A., Luxembourg (LU)

( * ) Notice: Subject to any disclaimer, the term of this patent is extended or adjusted under 35 U.S.C. 154(b) by 0 days.

(21) Appl. No.: 13/883,077

(22) PCT Filed: Oct. 21, 2011

(86) PCT No.: PCT/EP2011/068444
§ 371 (c)(1),
(2), (4) Date: May 2, 2013

(87) PCT Pub. No.: WO2012/059339
PCT Pub. Date: May 10, 2012

(65) Prior Publication Data
US 2013/0229658 A1  Sep. 5, 2013

(30) Foreign Application Priority Data
Nov. 4, 2010  (LU) .......................................... 91 752

(51) Int. Cl.
*G01N 21/39* (2006.01)
*G01N 21/3504* (2014.01)
*G01N 21/35* (2014.01)

(52) U.S. Cl.
USPC ..................................... 356/437; 250/339.07

(58) Field of Classification Search
CPC ..................................................... G01N 21/39
USPC ..................................... 356/437; 250/339.07
See application file for complete search history.

(56) References Cited

U.S. PATENT DOCUMENTS

2010/0140478 A1* 6/2010 Wilson et al. ............ 250/339.07

FOREIGN PATENT DOCUMENTS

| GB | 2418483 A | 3/2006 |
| WO | 0227297 A1 | 4/2002 |

OTHER PUBLICATIONS

International Search Report for corresponding application No. PCT/EP2011/06844 filed Oct. 21, 2011; Mail date Nov. 28, 2011.
Takaya Iseki, "A Compact Remote Methane Sensor using a Tunable Diode Laser" 20th International Laser Sensing Symposium, p. 2-7, May 17, 2008 XP002645931; Retrieved from internet: URL: http//www.lidar.nies.go.jp/LRSJ/20thLSS/P2-7.pdf.

(Continued)

Primary Examiner — Tarifur Chowdhury
Assistant Examiner — Md Rahman
(74) Attorney, Agent, or Firm — Cantor Colburn LLP

(57) ABSTRACT

A gas detector (100) for remote gas detection in a target region (106) comprises a light source (102) for emitting a light beam (110) into the target region and a light sensor (112) for sensing light returning therefrom. The light beam is wavelength-modulated around an absorption wavelength of the gas. A controller (108) is operatively connected to the light sensor for detecting a presence of the gas on a path of the light beam based on returning light sensed by the light sensor. An indicator (124) that is operatively connected to the controller indicates the presence of the gas. A scanning device (104) is arranged with respect to the light source so as to scan the light beam through the target region, and with respect to the light sensor so that the light sensor receives the returning light via the scanning device. The indicator cooperates with the scanning device to indicate a position of the gas in the target region.

16 Claims, 1 Drawing Sheet

(56) References Cited

OTHER PUBLICATIONS

Adam H, "Portable laser Gas Detector Systems for Landfill CH4 and CO2 Monitoring", 2008, pp. 1-2, XP002645940; Retrieved from internet: URL: http://www.envirotech-online.com/articles/gas-detection/8/hamish_adam_vp_sales_marketing_boreal_laser/portable_laser_gas_detector_systems_for_landfill_ch4_andco2_monitoring/398/.

Takaya Iseki, "Lasermethanetm A Portable Remote Methane Detector", R&D Division, Technology Development Dept., Sensing & Controls Center, Tokyo Gas Co., Ltd.

Written Opinion for corresponding application No. PCT/EP2011/06844 filed Oct. 21, 2011; Mail date Nov. 28, 2011.

* cited by examiner

GAS DETECTOR

TECHNICAL FIELD

The present invention generally relates to the field of remote detection of gas leaks. In particular, the invention relates to a gas detector, e.g. for use in industrial environment.

BACKGROUND ART

Some years ago, portable remote gas detectors have been developed for checking the presence of a gas leak from a distance by hand-scanning a laser beam across a target region. Such target region would typically be the neighborhood of a gas pipe or a gas pipe network. Portable remote methane detectors are e.g. available under the trademark Laser-Methane. These devices emit a laser beam and receive a fraction of backscatter from the target region to measure the concentration-length product of methane between the detector and the target. As explained in the paper "Laser-Methane™—A portable remote methane detector", by Takaya Iseki, the technique used is tunable diode laser absorption spectroscopy (TDLAS), more specifically second-harmonic detection of wavelength modulation spectroscopy (WMS). The interested reader may refer to that paper and the references cited therein to learn the details of that technique. The known person-portable gas detection device is equipped with a visible red laser pointer to show the point currently aimed at. When the presence of gas is detected in the checked direction, i.e. if the concentration-length product exceeds a predetermined threshold, the remote gas detection device issues an alarm signal to warn its user.

A disadvantage of the known remote gas detection device is that there is some risk for the operator to miss a leak because of an imperfect manual scan of the target area. Indeed, even a concentrated user could accidentally forget to point at some zones of As a consequence, the reliability of a leak detection campaign using the handheld gas detection device depends to a large extent on the completeness of the manual scan.

Another drawback of the known handheld gas detection device is that the manual scanning of large areas may take a long time.

BRIEF SUMMARY

A gas detector is proposed for remote detection that allows for more reliable detection of gas and has the potential of reducing the time needed for scanning a target region.

According to the invention, a gas detector for remote detection of a gas (e.g. methane, $CO_2$, CO, $N_2O$, ethanol, etc.) in a target region comprises a light source (e.g. a laser, preferably a tunable diode laser) for emitting a wavelength-modulated light beam into the target region and a light sensor, e.g. a photodiode, a photovoltaic detector, a photon drag detector (e.g. available from Hamamatsu), for sensing light returning from the target region. The light beam carries a wavelength modulation around an absorption wavelength of the gas. A controller (such as e.g. a microcontroller, an application-specific integrated circuit, a field-programmable gate array, or the like) is operatively connected to the light sensor for detecting a presence of the gas on a path of the wavelength-modulated light beam in the target region based on the returning light sensed by the light sensor. The gas detector comprises an indicator (e.g. for providing a visual, audible or vibratory alarm) that is operatively connected to the controller for indicating the presence of the gas. The gas detector comprises a scanning device, configured and arranged with respect to the light source for scanning the wavelength-modulated light beam emitted by the light source through the target region, and with respect to the light sensor in such a way that the light detector receives the light returning from the target region via the scanning device. The indicator is configured to cooperate with the scanning device to indicate a position of the gas in the target region.

Those skilled will appreciate that the gas detector according to the invention is configured for automatically scanning a target region. The scanning pattern (e.g. a Lissajous curve) is preferably sufficiently dense not to leave blank spots (i.e. spots that are not swept over by the light beam) in the target region. The density of the scanning pattern is preferably adjusted to the divergence of the light beam in order to achieve an efficient scan of the entire target region. Compared to a manual scan of the target region, an automatic scan has the advantages of repeatability, higher reliability and typically also a higher scanning speed. Those skilled will furthermore appreciate that the gas detector according to the invention may be implemented as a person-portable (e.g. handheld) device. Nevertheless, it could also be provided with a support (e.g. a tripod). An interesting advantage of the present invention is thus that, after it has been mounted in a strategic position, it can be used to monitor the target region autonomously. For such surveillance applications, the gas detector preferably comprises a communication device (e.g. a network interface controller, Bluetooth device, USB port, etc.) to connect to a surveillance center.

Preferably, the scanning device comprises a scanning mirror, which, in operation, sweeps the wavelength-modulated light beam through the target region and reflects the light returning from the target region to the light sensor. Such scanning mirror may comprise e.g. a two-axis resonance-type micro-mechanical mirror or two one-axis resonance-type micro-mechanical mirrors arranged with respect to one another so as to allow achieving a two-dimensional scan of the target region. In case the scanning device comprises two one-axis resonance-type micro-mechanical mirrors, one or more intermediary mirrors may be arranged on the optical path between the micro-mechanical mirrors.

According to a first preferred embodiment of the invention, the indicator comprises a light source (hereinafter called "second light source", for distinction from the first light source that emits the wavelength-modulated light beam) arranged for emitting a visible light beam substantially collinear with the wavelength-modulated light beam into the target region via the scanning mirror. More preferably, the visible light beam and the wavelength-modulated light beam are emitted in such a manner that they are superposed to each other in the target region. According to this embodiment, the controller is operatively connected to the second light source for modulating the intensity of the visible light beam depending on whether presence of the gas on a path of the wavelength-modulated light beam is detected or not. The second light source could be intensity-modulated, e.g. by being switched on and off by the controller. Alternatively or additionally, the second light source could include a shutter (e.g. a mechanical or an optical one) that opens and shuts under the control of the controller. The controller preferably switches the second light source on each time and as long as the returning light indicates the presence of gas. If gas concentration is sufficiently high for being detected in a portion of the scene only, that portion will be indicated to the operator by illumination with visible light. Portions with no or not detectable amounts of gas will not be illuminated with visible light because the second light source will be switched off as the scanning device scans these portions of the target region. The frame rate of the scanning device (i.e. the inverse of the time needed for one scanning cycle) is preferably chosen high enough (e.g. ≥20 Hz, more preferably ≥30 Hz and still more preferably ≥50 Hz) for a human operator to see no or only little flicker in the illuminated portion of the scene. The second light source is preferably a laser source. The optical system of the wavelength-modulated and/or the visible light beam is preferably configured in such a way that both light beams have the same or substantially the same divergence in the target region, whereby the spot illuminated with the visible light corresponds to the spot hit by the wavelength-modulated light beam.

The gas detector preferably comprises a beam combiner (e.g. a dichroic mirror or an optical prism) for making collinear or superposing the visible light beam and the wavelength-modulated light beam.

The controller may be operatively connected to the scanning device in order to control the scanning of the wavelength-modulated light beam. In this case, the controller could, for instance, dynamically adjust the scanning pattern depending on the distribution of gas detected.

According to a second preferred embodiment of the invention, the indicator may be configured to display (e.g. on a display screen, an LCD or the like) one or more directions, in which the controller has detected the presence of gas. The displayed direction(s) may be determined based on the position of the scanning device at the moment(s) when the presence of gas is detected. In particular, when the controller detects gas (e.g. by comparing the concentration-length product with a threshold) the current the position of the scanning device (e.g. the orientation of the scanning mirror(s) relative to the reference frame of the gas detector) is converted into a direction indication. The so-computed information may be displayed e.g. on the background of the target region and/or on an LCD, etc.

According to a third embodiment of the gas detector, the indicator comprises a second light source (e.g. a laser) for emitting a second light beam and a display (e.g. a diffusing screen, or a fluorescent screen, etc.). The scanning device is provided with a first and a second scanning mirror. The first scanning mirror achieves a two-dimensional scan of the target region with the wavelength-modulated light beam emitted by the light source, while the second scanning mirror scans the second light beam across the display with. The first and second scanning mirrors are configured to operate in synchronism (in such a way that there is a one-to-one correspondence between the positions of the first scanning mirror and the second scanning mirror, the correspondence remaining unchanged over time). The controller is operatively connected to the second light source to modulate the intensity of the second light beam (e.g. by switching the second light source on and off) depending on whether presence of the gas on a path of the wavelength-modulated light beam is detected or not. The second light beam creates a visible light spot on the display that indicates the position of the gas in the target region. Since the scanning mirrors are operated in synchronism, there According to a variant of the third embodiment of the gas detector, the first and second scanning mirrors are two-axis resonance-type micro-mechanical mirrors, i.e. both are able to tilt according to two axis and thus to perform a scan in two dimensions. Alternatively, each of the first and second scanning mirrors may comprise two one-axis resonance-type micro-mechanical mirrors arranged on with respect to the other in such a way that the light beam passing on the micro-mechanical mirrors can be swept in two dimensions.

Preferably, the display is back-illuminated with the second light beam.

In the third preferred embodiment, the second light beam may be an invisible light beam (e.g. UV or IR light) if the display is a fluorescent screen that absorbs the invisible light beam and emits visible light in turn. However, if no fluorescent screen is used, a visible light beam may be used to indicate the position of the gas.

To perform the intensity-modulation of the second light beam, the second light source may be switched on and off by the controller and/or comprise a shutter (e.g. a mechanical or optical one) that opens and obstructs the light path under the control of the controller.

Advantageously, the gas detector may comprise a deflection mirror to deflect light returning from the background of the target region onto the light sensor. The deflection mirror preferably has an opening, which the wavelength-modulated light beam and possibly the visible light beam pass through. Such deflection mirror is preferably curved to focus the returning light onto the light sensor.

It shall be noted that the wavelength-modulated light beam may also carry an amplitude modulation. This is preferably achieved by using, as the first light source, a laser whose wavelength and output power depend on the same control variable, e.g. the current used for driving the laser: by applying a sinusoidal modulation on the control variable, one obtains a sinusoidal modulation both in intensity and wavelength of the light beam. The nominal wavelength of the laser is adjusted to an absorption wavelength of the gas to be detected. The controller is then able to detect the gas by comparing, in the light returning from the target region, the power at the second-harmonic of the modulation-frequency (i.e. at twice the modulation frequency) with the power at the modulation-frequency itself. The concentration-length product may be obtained from the ratio of the power at the second-harmonic and the power at the modulation-frequency.

The gas detector may be configured to detect a single or a plurality of gas species. A user of the gas detector usually has to detect presence of gases that represent a potential danger, such as explosive gases (e.g. methane) or toxic gases.

BRIEF DESCRIPTION OF THE DRAWINGS

Preferred embodiments of the invention will now be described, by way of example, with reference to the accompanying drawings, in which.

DESCRIPTION OF PREFERRED EMBODIMENTS

Figure 1:
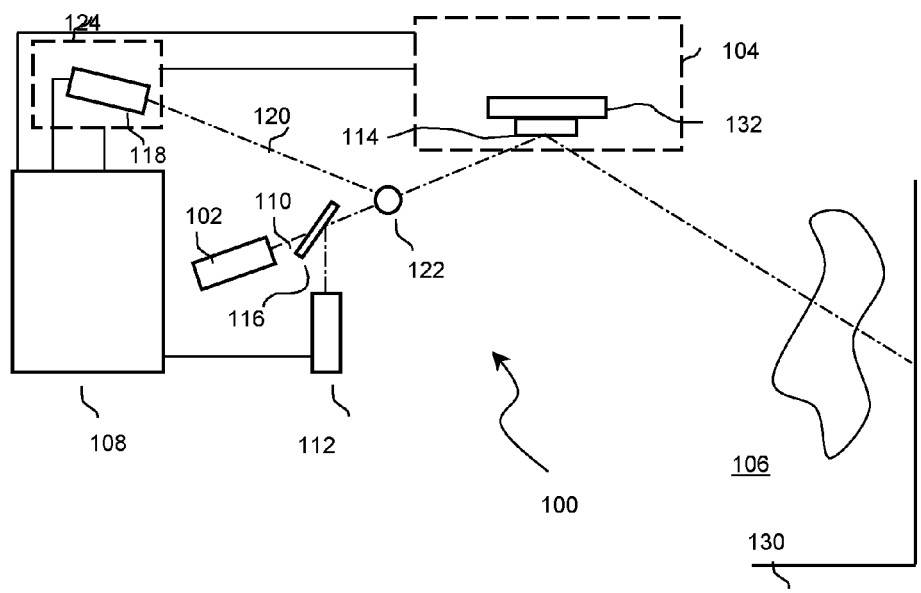
FIG. 1 is a block schematic diagram of a first embodiment of a gas detector.

FIG. 1 shows a first embodiment of a gas detector 100 for remote detection of a gas (e.g. methane) in a target region 106. The gas detector 100 comprises a first light source 102. Light source 102 is preferably a laser, e.g. a near-infrared tunable diode laser or an InGaAsP DFB laser, with a wavelength at an absorption line of the gas species to be detected (e.g. 1.6537 µm for the $2v_3$-band R(3) line of methane). The light source 102 is configured for emitting a wavelength-modulated light beam 110 via a scanning device 104 into the target region 106. The scanning device 104, which comprises a scanning mirror 114, is operatively connected to a controller 108 (e.g. a microprocessor, an application-specific integrated circuit, a field-programmable gate array or the like) for controlling the motion of the scanning mirror 114 and thus to scan the wavelength-modulated light beam 110 across the target region 106 according to certain scanning pattern. The wavelength-modulated light beam 110 is sinusoidally modulated in wavelength (around a center wavelength that corresponds to the absorption line of the gas to be detected) and amplitude. The amplitude modulation and the wavelength modulation are in phase with each other. When the wavelength-modulated light beam 110 hits an obstacle in the target region 106, part of the light is reflected and/or backscattered in the direction from which it came. The gas detector 100 comprises a light sensor 112 (e.g. a photodiode) that senses the fraction of light that returns from the target region 106 along the light path of the outbound light beam 110. Between the first light source and the scanning mirror 114, the wavelength modulated light beam 110 passes an opening (not shown in FIG. 1) in a static deflection mirror 116, which directs light that is scattered back from the target region 106 onto the light sensor 112. The deflection mirror 116 is preferably curved, so as to focus the backscattered light onto the light sensor. Additionally or alternatively, the gas detector 100 may comprise focusing optics arranged in front of the light sensor 112. The controller 108 is operatively connected to the light sensor 112 to receive a signal indicative of the light impinging on the light sensor 112.

When the wavelength-modulated light beam 110 (and the back-reflected fraction thereof) passes through a volume containing the gas to be detected, the gas will absorb a part of the photons whose wavelength corresponds to the absorption line. This induces an additional amplitude modulation at twice the original modulation frequency in the light that returns to the sensor. The controller 108 determines the power within the returning light at the modulation frequency, $P_{1f}$, and the power at the double modulation frequency, $P_{2f}$. The ratio $P_{2f}/P_{1f}$ is proportional to the concentration-length product in the direction currently aimed at by the scanning device. In order to decide whether gas is present in that direction, the controller 108 compares the concentration-length product with a predetermined threshold.

The gas detector 100 further comprises an indicator 124 operatively connected to the controller 108 to indicate the presence of gas to the operator. The indicator 124 comprises a second light source 118 in form of a laser capable of emitting a visible light beam 120. A beam combiner (e.g. a dichroic mirror, a prism or the like) is arranged in the light paths of the visible light beam 120 and the wavelength-modulated light beam 110 to combine (superpose) them before they are deflected by the scanning mirror 114 and are swept across the target region 106. The controller 108 keeps the second light source 118 switched off when no gas is detected in the target region 106 but switches it on as soon as and as long as the presence of gas is detected. Thus, whenever gas is detected in a certain direction, the gas detector 100 produces a bright spot on the background 130 of the target region 106 that allows the operator of the gas detector 100 to determine the regions in which the presence of gas has been ascertained. It should be noted that instead of switching the second light source off, the controller 108 could be configured and arranged to substantially dim the intensity of the visible light beam or to cause the visible light beam 120 to be blocked (using e.g. a mechanical or electronic shutter). The light sensor 112 and the controller 108 have to be sufficiently fast to allow the second light source to be switched on nearly instantaneously, since otherwise the visible spot could be significantly offset from its theoretical location. The detection may e.g. be achieved at a rate of about 100 KHz.

The beam combiner 122 is preferably a dichroic mirror i.e. it has significantly different reflection or transmission properties at the wavelengths of the visible light beam 120 and the wavelength-modulated light beam 110, respectively. In the configuration of FIG. 1, the beam combiner is transparent for the wavelength-modulated light beam 110 and the fraction thereof that returns from the target region, whereas it reflects the visible light beam 120. Alternatively, the beam combiner could be transparent for the visible light beam 120 and reflect the wavelength-modulated light beam 110 and the fraction thereof that returns from the target region.

The scanning mirror 114 is preferably a two-axes resonance-type micro-mechanical mirror or a similar device capable of two-dimensional scanning. However, there might be applications for which a one-dimensional scan of the scene is sufficient. In this case, a single-axis scanning mirror would be sufficient.

Figure 2:
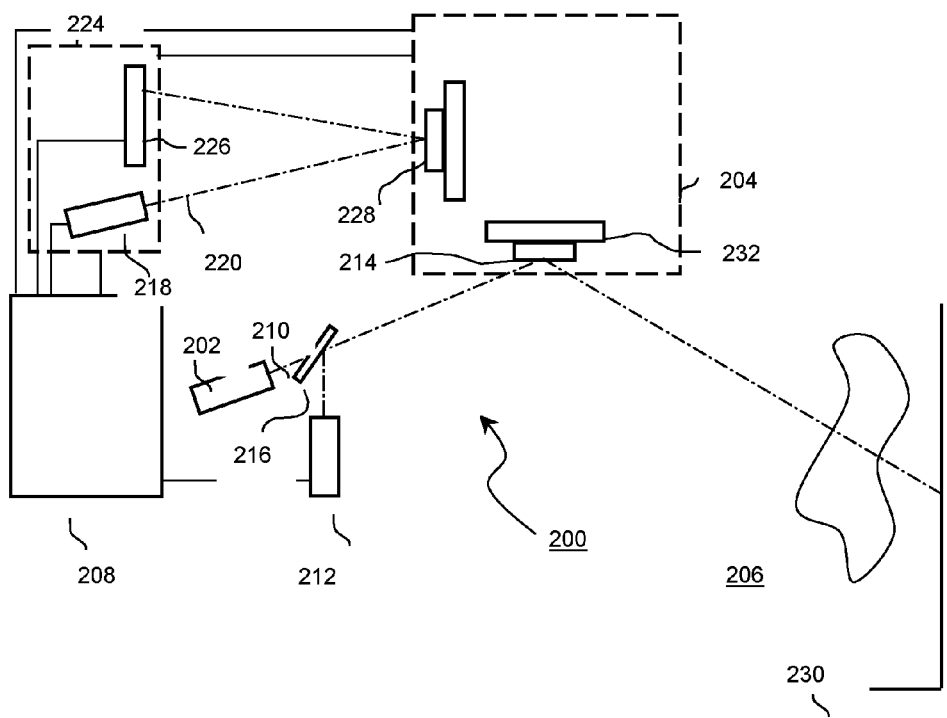
FIG. 2 is a block schematic diagram of a second embodiment of a gas detector.

FIG. 2 shows a second embodiment of a gas detector 200 for remote detection of gas in a target region 206. The gas detector 200 comprises a light source 202, for emitting a wavelength-modulated light beam 210 via a scanning device 204 into the target region 206. The scanning device 204 comprises a first scanning mirror 214 and is operatively connected to a controller 208 that controls sweeping the wavelength-modulated light beam 210 across the target region 206. A light sensor 212 (e.g. a photodiode) is provided for sensing the fraction of light that returns from the target region 206 along the light path of the outbound light beam 210. Between the first light source 202 and the scanning mirror 214, the wavelength modulated light beam 210 passes an opening (not shown in FIG. 2) in a static deflection mirror 216, which directs light that is scattered back from the target region 206 onto the light sensor 212. The controller 208 is operatively connected to the light sensor 212 to receive a signal indicative of the light impinging on the light sensor 212. In respect of the features of the gas detector 200 discussed so far, it operates in the same way as the gas detector 100 of FIG. 1. The differences are addressed hereinafter.

The gas detector 200 comprises an indicator 224 cooperating with the scanning device 204 to indicate the position of gas detected in the target region 206. The indicator 224 includes a light source 218 (e.g. a laser) and a display screen 226. The scanning device 204 comprises a second scanning mirror 228 that is driven in synchronism with the first scanning mirror 214 and that is arranged with respect to the second light source 218 and the display screen 226 in such a way that the light beam 220 emitted by the second light source (the "second light beam") is deflected by the second scanning mirror 228 onto the display screen 226. As the two scanning mirrors 214, 228 are operated in synchronism, there is a constant one-to-one correspondence between a spot created by the second light beam on the display screen and the direction into which the first light beam 210 is emitted. The second light source 218 is switched on and off under the control of the controller 218 that is operatively connected to the indicator 224. In particular, the controller 208 keeps the second light source 218 switched off when no gas is detected in the target region 106 but switches it on as soon as and as long as the presence of gas is detected. Thus, whenever gas is detected in a certain direction, the operator is presented a bright spot on the display screen 226 that indicates the direction(s) in which the presence of gas has been ascertained. The display screen 226 is advantageously provided with a graduated scale or the like to simplify the reading of the indications.

The display screen 226 is preferably a diffusive screen that allows an operator to view the bright spot from a broad viewing angle. The second light beam 220 may be a visible light beam or an invisible one. In the latter case, however, the display screen 226 needs to be configured in such a way that the invisible light is converted into visible light (e.g. by using a fluorescent screen).

While specific embodiments have been described in detail, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. A gas detector for remote detection of a gas in a target region, comprising
   a light source for emitting a wavelength-modulated light beam into said target region, said wavelength-modulated light beam carrying a wavelength modulation around an absorption wavelength of said gas,
   a light sensor for sensing light returning from said target region,
   a controller operatively connected to said light sensor for detecting a presence of said gas on a path of said wavelength-modulated light beam in said target region based on the returning light sensed by said light sensor,
   an indicator operatively connected to said controller for indicating said presence of said gas;
   wherein
   said gas detector comprises a scanning mirror, configured and arranged with respect to said light source for scanning said wavelength-modulated light beam, emitted by said light source, through said target region, and with respect to said light sensor in such a way that said light sensor receives said light returning from said target region via said scanning mirror,
   and wherein said indicator is configured to cooperate with said scanning mirror to indicate a position of said gas in said target region.

2. The gas detector as claimed in claim 1, wherein said indicator comprises a second light source arranged for emitting a visible light beam substantially collinear with said wavelength-modulated light beam into said target region via said scanning mirror, said controller being operatively connected to said second light source to modulate an intensity of said visible light beam depending on whether presence of said gas on a path of said wavelength-modulated light beam is detected or not.

3. The gas detector as claimed in claim 2, comprising a beam combiner for making said visible light beam and said wavelength-modulated light beam substantially collinear.

4. The gas detector as claimed in claim 1, wherein said scanning mirror is a resonance-type micro-mechanical mirror.

5. The gas detector as claimed in claim 1, wherein said controller is operatively connected to said scanning device to control said scanning of said wavelength-modulated light beam.

6. The gas detector as claimed in claim 5, wherein said indicator is configured to display one or more directions in which presence of gas is detected by said controller based on a position of said scanning device when presence of gas is detected.

7. The gas detector as claimed in claim 1, comprising a deflection mirror to deflect said returning light to said light sensor, said deflection mirror having an opening, which said wavelength-modulated light beam is made to pass through.

8. The gas detector as claimed in claim 1, wherein said wavelength-modulated light beam also carries an amplitude modulation.

9. The gas detector as claimed in claim 1, wherein said absorption wavelength is an absorption wavelength of at least one of methane, ethanol, $CO_2$, $CO$ and $N_2O$.

10. A gas detector for remote detection of a gas in a target region, comprising a light source for emitting a wavelength-modulated light beam into said target region, said wavelength-modulated light beam carrying a wavelength modulation around an absorption wavelength of said gas, a light sensor for sensing light returning from said target region, a controller operatively connected to said light sensor for detecting a presence of said gas on a path of said wavelength-modulated light beam in said target region based on the returning light sensed by said light sensor, an indicator operatively connected to said controller for indicating said presence of said gas; wherein said gas detector comprises a scanning device, configured and arranged with respect to said light source for scanning said wavelength-modulated light beam, emitted by said light source, through said target region, and with respect to said light sensor in such a way that said light sensor receives said light returning from said target region via said scanning device, wherein said indicator is configured to cooperate with said scanning mirror to indicate a position of said gas in said target region, said indicator comprising a second light source for emitting a second light beam and a display, wherein said scanning device comprises a first scanning mirror for scanning said wavelength-modulated light beam through said target region and for reflecting said light returning from said target to said light sensor and a second scanning mirror for scanning said second light beam across said display in synchronism, said first and second scanning mirrors being configured for operating in synchronism, said controller being operatively connected to said second light source to modulate an intensity of said second light beam depending on whether presence of said gas on a path of said wavelength-modulated light beam is detected or not.

11. The gas detector as claimed in claim 10, wherein said first and second scanning mirrors are resonance-type micromechanical mirrors.

12. The gas detector as claimed in claim 10, wherein said display is back-illuminated with said second light beam.

13. The gas detector as claimed in claim 10, wherein said second light beam is an invisible light beam and wherein said display is configured to absorb said invisible light beam and emit visible light.

14. The gas detector as claimed in claim 10, comprising a deflection mirror to deflect said returning light to said light sensor, said deflection mirror having an opening, which said wavelength-modulated light beam is made to pass through.

15. The gas detector as claimed in claim 10, wherein said wavelength-modulated light beam also carries an amplitude modulation.

16. The gas detector as claimed in claim 10, wherein said absorption wavelength is an absorption wavelength of at least one of methane, ethanol, $CO_2$, $CO$ and $N_2O$.

* * * * *